(12) United States Patent
Petrigni et al.

(10) Patent No.: US 7,060,691 B2
(45) Date of Patent: Jun. 13, 2006

(54) PHARMACEUTICAL COLLOIDAL PREPARATION USEFUL IN THE TREATMENT OF RESPIRATORY DISEASES

(76) Inventors: Giuseppe Petrigni, Milano via Fontana (IT); Luigi Allegra, Milano via DeAmicis (IT)

( * ) Notice: Subject to any disclaimer, the term of this patent is extended or adjusted under 35 U.S.C. 154(b) by 0 days.

(21) Appl. No.: 10/267,863

(22) Filed: Oct. 10, 2002

(65) Prior Publication Data

US 2004/0071740 A1 Apr. 15, 2004

(51) Int. Cl.
*A61K 31/70* (2006.01)
(52) U.S. Cl. .......................................... 514/54
(58) Field of Classification Search .................. 514/54
See application file for complete search history.

(56) References Cited

U.S. PATENT DOCUMENTS 6,383,344 B1 * 5/2002 Miller et al. ............. 204/157.6

FOREIGN PATENT DOCUMENTS

WO WO 95/26735 * 10/1995

* cited by examiner

*Primary Examiner*—Elli Peselev
(74) *Attorney, Agent, or Firm*—Michael G. Gilman

(57) ABSTRACT

A pharmaceutical colloidal preparation useful in the treatment of diseases of the upper and lower respiratory tract, and lung parenchyma which contains, as an active ingredient, a colloidal mixture of hyaluronic acids of different molecular weights, in addition to a suitable diluent is described.

16 Claims, No Drawings

PHARMACEUTICAL COLLOIDAL PREPARATION USEFUL IN THE TREATMENT OF RESPIRATORY DISEASES

The present invention relates to a colloidal pharmaceutical preparation useful in the treatment of diseases of the upper and lower respiratory tract, and lung parenchyma.

The pharmaceutical preparation object of the present invention contains, as an active ingredient, a colloidal mixture of hyaluronic acids of different molecular weights, in addition to a suitable diluent. The preparation has shown to be particularly effective in the treatment of diseases of the upper and lower airways, and the lung parenchyma.

Another object of the present invention is the use, in diseases of the upper and lower airways, and the lung parenchyma, of the colloidal preparation, consisting of a mixture of hyaluronic acids of different molecular weights, optionally additioned to a suitable diluent, by systemic, oral and topical administration.

The preparation object of the present invention is preferably administered locally in aerosol form, within the airways by means of nebulisers, spray, or in the form of inhalatory powder or it may be substituted and/or integrated by local instillation. The preparation is also suitable for systemic administration, by means of subcutaneous, intramuscular, intradermic injection, or oral administration in the form of tablets, or transculaneously by means of skin patches. For specific therapeutic indications, systemic administration may be added to topical inhalation or instillation.

A further object of the present invention is the process employed to obtain the preparation of the present invention which contains a suitable mixture of different molecular weight hyaluronic acids, as active ingredients, in addition to a suitable diluent, that has shown to be effective in the treatment of diseases of the upper and lower respiratory tract, and the lung parenchyma.

BACKGROUND OF THE INVENTION

Hyaluronic acid is a naturally occurring biopolymer exerting numerous biological activities in bacteria and more complex animal organisms, including man. Naturally occurring hyaluronic acid may be found in highly evolved animal tissues, mostly present in intercellular spaces. It may be found in practically every part of living organisms, its distribution being almost ubiquitous in tissues and in organ parenchyma, reaching greater concentration in lax connective tissue and specifically in vitreous humour and joint synovial fluid. The serum levels of hyaluronic acid are generally between 10 and 100 µg/L. The lung content of the different forms of hyaluronic acid varies between 15 and 170 µg/gr of dry weight. Lung hyaluronic acid is primarily found in perialveolar and peribronchial tissue. It is drained through the lymphatic system and finally broken down in hepatic lymph nodes. Up to a short time ago, hyaluronic acid was traditionally derived from natural deposits such as cockscomb, or bovine connective tissue by separation methods consisting of an enzyme digestion, a specific separation intended to remove the proteins and a purification to obtain the crude extract. These methods present several disadvantages connected to high production costs, poor control over molecular weight, and risk of viral infection.

Hyaluronic acid may also be produced by means of bio-fermentation. Biotechnological processes such as Gram-positive bacterial fermentation have recently been used: this technique allows the formation of potentially unlimited resources of hyaluronic acid biopolymers devoid of the aforementioned drawbacks. A mucous capsule of hyaluronic acid envelops Streptococci (Gram-positive bacteria). Hyaluronic acid produced by streptococcal fermentation varies in molecular weight from 1 to 4 MDa.

Hyaluronic acid is a member of the glycosaminoglycan family, composed of linear, non-ramified, disaccharide polyanionic chains wherein disaccharide units, composed of n-acetylglucosamine and glucuronic acid, bonded each other by glucoside links, are repeat structures. Hyaluronic acid molecular weight may vary from hundreds of thousands to millions of Daltons. Unlike other glycosaminoglycans, hyaluronic acid contains no sulphate groups, is free from covalent bonds with proteins, and is thought to possess, amongst all mucopolysaccharide substances, the simplest chemical structure.

In body tissues, hyaluronic acid is found bound to cell membranes, joined to other macromolecules, or as a free polysaccharide. It is unique in its ability to bond and retain large amounts of water in the interfibrillar spaces—up to 6 liters of water per gram of hyaluronic acid—thus forming the backbone of the amorphous colloidal matrix acting as cement between cells and connective fibers. As a result of its influence on interstitial volume, water conductivity and macromolecule diffusion, hyaluronic acid plays a significant effect in regulating microcirculatory exchanges.

Within the skin, solutions of hyaluronic acid in water give rise to gels that act as dampers. Hyaluronic acid plays an important role in the body, both for its mechanical and transport properties. It has shown to be important in different tissue functions such as hydration, lubrication, solute transport, cell detachment and migration. Hyaluronic acid also plays a central role in controlling cell growth and differentiation in addition to tissue morphogenesis. Hyaluronic acid solutions are typically viscoelastic and pseudoplastic. The viscoelastic properties of hyaluronic acid, important in its use as a biomaterial, are determined by the concentration and molecular weight of its chains. The molecular weight of the different forms of hyaluronic acid is polydispersed and highly variable, ranging between 10,000 and 10,000.000 Da.

Bronchial asthma is a disease displaying acute reversible bronchoconstriction associated with airway inflammation and hyper-responsiveness leading to excessive bronchospasm in response to a variety of external stimuli that may be specific (allergens), non specific chemicals (histamine, metacholine), or physical agents (ultasound nebulized water, cold air, polluting gases). It is a well known fact that hyaluronic acid is currently used in many fields of medicine: it is employed in different settings such as orthopaedics and surgery. The use of hyaluronic acid in the treatment of diseases of the respiratory tract, specifically involving the lung and bronchi, is described in the International Patent Application WO 95/26735; salt, alcohol, aqueous, or dimethylsulphoxide solutions of hyaluronic acid are administered in the trachea of experimental animals at a daily dose between 10 µg/kg and 2 mg/kg.

DESCRIPTION OF THE INVENTION

It has been found, and this is the object of the present invention, that colloidal pharmaceutical preparations containing hyaluronic acid biopolymers, having different molecular weight and suitably mixed each other in a proper ratio and dispersed in a suitable diluent, showed to be very effective in the treatment of diseases of the upper and lower airways, and the lung parenchyma.

In particular among the diseases of the airways are included: tonsillitis, pharyngitis-laringitis-trachcatis, nasal polyps, vocal chord polyps, sinus polyposis, acute and chronic rhinitis, allergic rhinitis, vasomotor rhinitis, otitis, diseases of the sinuses, allergic and non allergic bronchial asthma, both simple and obstructive chronic bronchitis, chronic obstructive pulmonary disease (COPD), primary and secondary pulmonary emphysema, usual interstitial pneumonitis, fibrosing alveoltis, interstitial fibrosis of both known and unknown origin, vascular and bronchial pulmonary dysplasia, bronchiectasis, pulmonary manifestations of collagen diseases, work related pulmonary diseases, both primitive (carcinoma and sarcoma) and metastatic lung tumours, neoplasms of the pleura, pneumonia (bacterial, viral, fungal, parasitic), irritant-related (gas or chemical) lung injury, primary and metastatic diseases of the pleura, ARDS and IRDS (Adult and Respiratory Distress Syndrome), pulmonary tuberculosis, pulmonary embolism and infarction, cartilage diseases involving the larynx, the trachea, or the bronchi, upper and lower airway vascular diseases, neurogenic diseases of the upper and lower airways, muscular-tendon diseases of the upper and lower airways, pulmonary mycosis.

Examples of suitable diluents of the mixture of hyaluronic acids are distilled water, saline, dimethylsulfoxide, or alcohol solutions.

More specifically, hyaluronic acids or hyaluronic fractions forming the mixture of the invention have a molecular weight comprised in the range from 50 kDa and 4,000 kDa. The fractions are mixed in defined proportions on the basis of their respective molecular weights Among the preferred pharmaceutical preparations of the present invention are mixtures containing hyaluronic acids having molecular weight values representing multiples, in respect to the molecular weight of the lowest molecular weight component, the different molecular weight hyaluronic acids being optionally each other in a unitary ratio. Generally, the number of hyaluronic acids of different molecular weight contained in the mixture may vary considerably and also may vary the ratio in which the different molecular weight hyaluronic acids are each other mixed in the mixture. Preferably the number of different molecular weight hyaluronic acids present in the mixture varies from 2 to 9, and more preferably from 5 to 7.

Preferred mixtures of hyaluronic acids are those containing 100 kDa and 400 kDa hyaluronic acids and optionally their multiples: among them are particularly preferred those mixtures of hyaluronic acids having molecular weight: 100 kDa, 200 kDa, 400 kDa, 800 kDa, 1,200 kDa and those mixtures of hyaluronic acids having molecular weight: 400 kDa, 800 kDa, 1,200 kDa, 1,600 kDa and 2,000 kDa.

Synthesis Scheme for a 10% Hyaluronic Acid Colloidal Preparation (Hereafter Defined as Preparation A).

Solutions of hyaluronic acid with molecular weight ranging between 200 and 4,000 kDa were prepared. The process of preparation is essentially based on the condensation reaction between plant-extracted glucuronic acid and a solution of hydrolysed chitine (85–90% of dry acetylglucosamine), in the presence of a biological catalyst, at a temperature of 8–20° C. A disaccharide mixture, 90% of which, in dry weight, having substantially a structure identical to that of the hyaluronic acid basic monomer, and 10%, in dry weight being the polymers, up to 4,000 kDa, of the basic monomer, is obtained. The mixture, in the form of a 10% aqueous solution, is a transparent colloidal fluid. The above mentioned proportions between monomers and polymers were chosen in order to optimize the degree of viscosity without interfering with the required activities of the preparation.

Pour 890 g of demineralized water into a steel turboemulsor, bring the temperature of the fusor to 18–20° C. and create a vacuum. Start the mixer at low speed and, after having controlled the temperature (18–20° C.), slowly add 100 g of the hyaluronic acid mixture and 10 g of methyl parabenzoate. The mass obtained is then homogenized at low speed for approximately 5 minutes. Once the product is homogenized, the mixer is kept running for an extra 30 minutes. The resulting product is kept under vacuum for 60 minutes, and the apparatus then discharged.

With the aid of a mucorheometer device (Eslab, Milan, Italy), viscosity (h) and elasticity (G) of preparation A were evaluated at different temperatures. No correlation was found between temperature and elasticity, whereas an inverse correlation was demonstrated between viscosity and temperature, considering that the preparation was obtained at 18–20° C. Elongability (spinnability) values of preparation A were also determined.

| Viscosity (h): | | |
|---|---|---|
| at 5° C. | h(mPas) | 7200.20 (immediate) |
| | h(mPas) | 6446.77 (after 5 minutes) |
| at 21° C. | h(mPas) | 6001.79 (immediate) |
| | h(mPas) | 5931.37 (after 5 minutes) |
| at 37° C. | h(mPas) | 5676.34 (immediate) |
| | h(mPas) | 5642.63 (after 5 minutes) |

Spinnability: at room temperature=18 mn

Synthesis Scheme for a 4.5% Hyaluronic Acid Colloidal Preparation (Hereafter Defined as Preparation B).

The procedure is similar to the above-described one, using 950 g of demineralized water, 45 g of the hyaluronic acid mixture, and 5 g of methyl parabenzoate. The colloidal preparation B showed the following viscosity (h) values:

| at 37° C. | h(mPas) | 95.79 (immediate) |
|---|---|---|
| | h(mPas) | 77.93 (after 5 minutes). |

Spinnability: at room temperature=5 mm

The preparation object of the invention is preferably administered locally in aerosol form, with the aid of a nebulizer or spray, but it may be instilled locally or administered systemically. The therapeutic dose of hyaluronic acid delivered varies according to age, patient conditions, and route of administration. The therapeutic dose for aerosol administration varies between 20 mg/kg and 0.2 mg/kg daily.

In the following Tables are given the relevant data obtained from clinical trials performed in asthmatic patients by means of aerosol administration using a pneumatic aerosol device (Nuovo Nebula, Markos, Monza, Italy or Clemny, Chiesi Parma, Italy). Specifically have been examined:

a 10% colloidal preparation (preparation A), nebulizing 1 mL, diluted to 5 mL by adding saline solution, obtaining a final concentration of 2%, and a 4.5% colloidal preparation (preparation B), nebulizing 1 mL, diluted to 4 mL by adding saline solution, reaching a final concentration of 1.125%.

The aerosol granulometry of the former colloidal preparation (10%) has been tested by diluting the preparation 50, 100, 150 fold in saline solution. An API aersizer apparatus (Amherst, Mass., USA) was employed.

A bimodal granulometry distribution was detected as shown by an "irregular" Gauss curve for aerosols with granules between 8 and 30μ in diameter (presumably involved in the drug's activity along the upper airways) and a "regular" Gauss curve for granules ranging 0.8–4μ in diameter (presumably active along the lower airways and the lung parenchyma).

Differences in the granulometric distribution were also detected using the pneumatic aerosolizer Nebula Nuovo compared to other devices, in addition to differences related to the use of different vials on the same device, and related to whether the "bell" technique was used or not. Therefore, in order to optimize hyaluronic acid therapeutic aerosol administration, studies are needed to precisely identify the anatomical targets to be reached so as to employ the aerosol device and accessories most suitably indicated for the clinical conditions of the patient and the desired therapeutic goal.

I) Protective Efficacy Towards the Bronchoconstrictive Effects of Different Non Specific Challenges (Non Allergic) in Asthmatic Patients.

The protective effects towards bronchoconstriction induced by specific and non specific challenges (Allegra L., Braga P C., Dal Negro R. Methods in Asthmology, Springer, Berlin & Milan, 1996) has been evaluated by using:

(1) exercise testing by means of a 1,000 m run to be performed within 10 minutes. The test was carried out on subjects with baseline $FEV_1$ values≧80% of predicted values.

(2) ultrasound nebulized distilled water challenge; inhalation of a nebulised hypotonic solution (distilled water) obtained by means of a 4 minute ultrasonic aerosol device. The test was carried out on subjects with baseline $FEV_1$ values≧80% of predicted values.

(3) metacholine challenge: aerosol administration of metacholine at geometrically progressive increasing doses. The test was interrupted once the $PD_{20}FEV_1$ (dose of metacholine capable of reducing $FEV_1$ values by 20% compared to baseline) was reached, and the value was recorded in μg/mL. Each aerosol metacholine dose was administered immediately following the previous dose. The test was performed on subjects with baseline $FEV_1$ values≧80% of predicted values.

(4) Specific bronchial provocation challenge with specific allergens: administration of Dermatophagoides pteronyssinus in patients with house dust mite-induced rhinitis or asthma. The test was performed on subjects with baseline $FEV_1$ values>80% of predicted values. Exercise testing (1) was performed, on two non-consecutive days, on 19 patients (16 males). Patients were pre-treated 30 minutes before the test with placebo (9% saline solution) or with preparation A aerosol administration. The study was performed in a randomized, cross-over, single blind fashion. Among the patients, 6 males were aged between 4 and 12 years; 6 males were aged between 13 and 16 years, and the remaining 7 patients (4 males and 3 females) were aged between 20 and 36 years.

Table 1 shows variations in $FEV_1$±s.e. (liters), as this is generally considered the most significant spirometric variable. For all 19 patients, spirometry values were obtained 5 minutes following termination of exercise testing.

TABLE 1

Exercise testing: evaluation of the efficacy of preparation A

| | Pre-treatment | | | |
|---|---|---|---|---|
| | Placebo | | Hyaluronic acid (preparation A) | |
| | Baseline | After challenge | Baseline | After challenge |
| $FEV_1$ (L) | 3.03 | 2.00 (−34%) | 2.98 | 2.60 (−13%) |
| Mean ± s.e. | ±0.24* | ±0.24# | ±0.25* | ±0.22# |
| P | <0.01 | | <0.01 | |

*p = NS
p = <0.01

Following stratification based on age in years, the bronchoconstrictive effect of exercise testing was found to be statistically relevant in children, adolescents, and adults (p<0.01 within each subgroup). The protective efficacy of the tested hyaluronic acid colloidal preparation, compared to placebo was equally statistically significant in all three age groups (p<0.02 for adolescents and adults, p<0.01 in children).

Ultrasonically nebulized distilled water testing (2) was performed, on two non-consecutive days, on 20 patients (13 males), aged between 15 and 62 years. Patients were pre-treated 30 minutes before the test with placebo (9% saline solution) or with preparation A aerosol administration. The study was performed in a randomized, crossover, single blind fashion. Table 2 shows variations in $FEV_1$±s.e. (liters), obtained for all 20 patients, 3–5 minutes following termination of challenge testing.

TABLE 2

Ultrasonically nebulized distilled water challenge: evaluation of the efficacy of preparation A.

| | Pre-treatment | | | |
|---|---|---|---|---|
| | Placebo | | Hyaluronic acid (preparation A) | |
| | Baseline | After challenge | Baseline | After challenge |
| $FEV_1$ (L) | 3.65 | 2.39 (−35%) | 3.68 | 2.78 (−24%) |
| Mean ± s.e. | ±0.17* | ±0.17# | ±0.18* | ±0.19# |
| P | <0.001 | | <0.01 | |

*p = NS
p = <0.05

Using the same ultrasonically nebulized distilled water challenge (2) on two non-consecutive days, 6 patients (5 males), aged between 18 and 46 years were examined. Patients were pre-treated 30 minutes before the test with placebo (9% saline solution) or with preparation B aerosol administration. The study was performed in a randomized, crossover, single blind fashion.

Table 3 shows variations in $FEV_1 \pm s.e.$ (liters), obtained for all 6 patients, 3–5 minutes following termination of challenge testing.

TABLE 3

Ultrasonically nebulized distilled water challenge: evaluation of the efficacy of preparation B.

| | Pre-treatment | | | |
|---|---|---|---|---|
| | Placebo | | Hyaluronic acid (preparation B) | |
| | Baseline | After challenge | Baseline | After challenge |
| $FEV_1$ (L) | 4.04 | 2.81 (−30%) | 4.05 | 3.38 (−16%) |
| Mean ± s.e. | (0.31* | ±0.30# | ±0.28* | ±0.31 |
| p | | <0.01 | | <0.01 |

*p = NS
p = <0.01

Metacholine challenge was performed, on two non-consecutive days, on 10 patients (6 males), aged between 18 and 54 years. Patients were pre-treated 30 minutes before the test with placebo (9% saline solution) or with preparation A aerosol administration. The study was performed in a randomized, cross-over, single blind fashion.

TABLE 4

Metacholine challenge: evaluation of the efficacy of preparation A

| | Pre-treatment | |
|---|---|---|
| | Placebo | Hyaluronic acid (preparation A) |
| $PD_{20}$ $FEV_1$ | 185 ± 29 | 789 ± 290 (+332) |
| p | | <0.03 |

The mixture of hyaluronic acids, named preparation A, was tested on 49 asthmatic patients (35 males, 14 females), and preparation B was tested on 6 asthmatic patients (5 males and 1 female). Both aerosol preparations were administered 30 minutes prior to patient exposure to non specific challenges (exercise in 19 patients; ultrasonic nebulized distilled water in 26 patients; increasing doses of aerosolized metacholine in 10 patients). Among these asthmatic patients, some had extrinsic asthma, whereas others had multifactorial forms of the disease. In all patients, both preparations A and B proved to be effective, with non detectable differences between patients with different forms of asthma. The doses employed were significantly protective in all cases, both in terms of spirometric parameters (as shown by $FEV_1$ values) in exercise testing and ultrasonically nebulized distilled water testing, and in terms of the dose of bronchoconstrictive substance (metacholine) required to reduce the $FEV_1$ values by 20% compared to baseline ($PD_{20}$). Preparation A was shown to be particularly effective during exercise and metacholine testing. Considering exercise testing, it must be added that the protection was statistically significant in all categories obtained by stratifying patients undergoing exercise testing: "children", "adolescents", and "adults". Moreover, for ultrasonically nebulized distilled water challenge, preparation B proved to be as protective as preparation A.

II) Protective Effects Towards the Bronchoconstrictive Effects of Specific Challenge (Allergen) in Asthmatic Patients.

Allergen testing was performed on 2 patients (1 male, 1 female) aged 16 and 26 years, with documented allergy to Dermatophagoides pteronyssinus (Dpt). The patients first underwent respiratory function testing, and hence specific bronchial provocation testing by nebulising 120 μg of the allergen (Dpt). Both patients were pre-treated on two non-consecutive days with placebo (9% NaCl solution) or hyaluronic acid (preparation B) aerosol 30 minutes prior to testing. Repeat $FEV_1$ determinations at 1; 5; 15: 30 minutes were performed following challenge termination. For the first patient the point of greatest "drop" in $FEV_1$ (after placebo pre-treatment) was observed at +5 minutes post-challenge, and at +30 minutes post-challenge for the second patient. Preparation B offered complete protection for the patients, given that in both cases it was not associated with the fall in $FEV_1$ observed following placebo pre-treatment.

III) Protective Efficacy Towards the Obstructive Effects on Nasal Airways Induced by Specific Challenge (Allergen) in Patients with Rhinitis.

It was demonstrated the protective effects towards nasal obstruction induced by specific challenge in patients with allergic rhinitis towards house dust mite by means of intranasal spray administration of *Dermatophagoides pteronyssinus,* 60 μg per nostril. Rhiomanometry was then performed Four patients (3 males) aged between 16 and 31 years underwent the above challenge following pre-treatment, on two non-consecutive days, 30 minutes before the test with placebo (9% NaCl solution) or with preparation B intranasal aerosol administration. Repeat rhiomanometry testing was performed to evaluate cumulative airflow across both nostrils at 1; 5; 15; 30; 60 minutes from termination of the challenge, in a randomized, cross-over, single blind fashion.

Table 5 shows variations in the most relevant rhiomanometry index, i.e. cumulative airflow (L $min^{-1}$)+s.c. across both nostrils during the expiratory phase of a normal respiratory cycle (at a constant pressure of 75 mPs), calculated as the maximal drop in airflow during the first 60 minutes following inhalation of placebo or preparation B.

TABLE 5

Intranasal inhalation of specific allergen challenge. Evaluation of the protective effects of preparation B. (cumulative expiratory flow for both nostrils in L.$min^{-1}$)

| | Pre-treatment | | | |
|---|---|---|---|---|
| | Placebo | | Hyaluronic acid (preparation B) | |
| | Baseline | Post-Dpt | Baseline | Post-Dpt |
| Case 1 | 599 | 63 | 987 | 626 |
| Case 2 | 427 | 189 | 225 | 247 |
| Case 3 | 525 | 254 | 403 | 470 |
| Case 4 | 185 | 25 | 932 | 484 |
| Mean ± s.e. | 434 ± 90 | 133 ± 53 | 637 ± 190 | 457 ± 78 |
| p | <0.01 | | NS | |

The invention claimed is:

1. An aerosolized colloidal suspension that is active for the treatment of at least one of respiratory diseases of the upper airways, bronchial asthma, chronic obstructive bronchitis and interstitial lung fibrosis, wherein said suspension comprises at least one diluent, and a plurality of hyaluronic acid biopolymer aliquots, wherein the hyaluronic acids have a plurality of different specific molecular weights that are multiples of the molecular weight of the lowest molecular weight hyaluronic acid present in the mixture, wherein the overall range of molecular weights of all of said hyaluronic acid is about 50 kDa to 1,200 kDa and wherein the hyaluronic acids comprise particles of about 0.8 to 4μ in diameter.

2. The aerosolized colloidal suspension according to claim 1, wherein the number of hyaluronic acids moieties having different molecular weights is about 2 to 9.

3. The aerosolized colloidal suspension according to claim 1 wherein the number of hyaluronic acid moieties having different molecular weights is about 5 to 7.

4. The aerosolized colloidal suspension according to claim 2, comprising a mixture of a plurality of hyaluronic acid moieties having, respectively, molecular weights of about 400, 800, and 1200kDa.

5. The aerosolized colloidal suspension according to claim 3 comprising a mixture of a plurality of hyaluronic acids moieties having, respectively, molecular weights of about 100, 200, 400, 800, and 1,200 kDa.

6. The aerosolized colloidal suspension as claimed in claim 1, wherein the hyaluronic acid moieties are suspended in at least one material selected from the group consisting of water, saline, dimethyl sulfoxide and an alcohol.

7. The aerosolized colloidal suspension according to claim 4 wherein the different byaluronic acid moieties in the suspension are in a reciprocal a ratio of about 1:1:1.

8. The aerosolized colloidal suspension according to claim 5 wherein the different hyaluronic acid moieties in the suspension are in a reciprocal ratio of about 1:1:1:1:1.

9. A method of treating at least one respiratory ailment of the upper respiratory tracts, bronchial asthma, chronic obstructive bronchitis and interstitial lung fibrosis, of an animal comprising administering to the animal in need thereof an effective amount of the aerosolized colloidal suspension as claimed in claim 1 for a period of time long enough to ameliorate the adverse effects of said ailment.

10. A method as claimed in claim 9 wherein said animal is human.

11. A method of treating at least one respiratory ailments of the upper respiratory airway, bronchial asthma, chronic obstructive bronchitis and interstitial lung fibrosis comprising administering to a patient in need thereof an effective amount of the aerosolized colloidal suspension as claimed in claim 4 for a period of time long enough to ameliorate the adverse effects of said ailment.

12. A method of treating at least one respiratory ailments of the upper respiratory airway, bronchial asthma, chronic obstructive bronchitis and interstitial Iwig fibrosis comprising administering to a patient in need thereof an effective amount of an aerosolized colloidal suspension as claimed in claim 7 for a period of time long enough to ameliorate the adverse effects of said ailment.

13. An aerosolized pharmaceutical colloidal suspension that is active for the treatment of respiratory diseases of the upper airways, and bronchial asthma, chronic obstructive bronchitis and interstitial lung fibrosis, wherein said suspension is in an aerosolized colloidal suspension form, and comprises at least one diluent, and a plurality of hyaluronic acid biopolymer moieties having the hyaluronic acid molecular weights in the range of about 50 kDa to 1,200 kDa; wherein each of the plurality of moieties has a different molecular weight and wherein the plurality of molecular weights are multiples of the molecular weight of the lowest molecular weight moiety and increasing in a multiple fashion to the highest molecular weight moiety and wherein said byaluronic acid moieties have particles having a bimodal distribution of diameters of about 0.8 to 4 µ and 8 to 30 µ, respectively.

14. A method of treating an ailment of at least the upper airway and bronchial asthma, chronic obstructive bronchitis and interstitial lung fibrosis that comprises administering to a patient in need thereof an effective amount of at least one aerosolized suspension as claimed in claim 13 for a time sufficient to ameliorate the adverse effects of said ailment.

15. The aerosolized colloidal suspension according to claim 1, wherein the molecular weights of said hyaluronic acid moieties are upto about 1,000 kDa.

16. The method as claimed in claim 9 wherein said mixture of hyaluronic acid moieties has molecular weights of up to about 1,000 kDa.

* * * * *

UNITED STATES PATENT AND TRADEMARK OFFICE
CERTIFICATE OF CORRECTION

PATENT NO. : 7,060,691 B2
APPLICATION NO. : 10/267863
DATED : June 13, 2006
INVENTOR(S) : Giuseppe Petrigni et al.

It is certified that error appears in the above-identified patent and that said Letters Patent is hereby corrected as shown below:

Column 1, line 27, change "transculaneously" to --transcutaneously--

Column 2, line 67, change "trachcatis" to --tracheitis--

Column 3, line 15, before "Respiratory" insert --Infant--

Column 3, line 61, change "8" to --18--;

Column 3, line 61, and Column 4, lines 5, 7, 27, 28, 29 and 43 change "° C." to --° C--;

Column 4, line 33, change "mn" to --mm--;

Column 5, line 54 and column 8, line 1 change "Dermatophagoides pteronyssinus" to --<u>Dermatophagoides pteronyssinus</u>--

Column 5, line 60, column 6, lines 37 and 65, column 7, line 23 and column 8, lines 5 and 27 change "%" to --‰--

Column 7, line 16, change "(0.31" to --± 0.31*--;

Column 8, line 22, change "*Dermatophagoides pteronyssinus*" to --<u>Dermatophagoides pteronyssinus</u>--;

Column 8, lines 23, 28, and 32, change "rhiomanometry" to --rhinomanometry--;

Column 8, line 33, change "+ s.c." to --+ s.e.--;

Column 8, line 58, change "airways" to --airway--;

Column 9, line 2, change "acids" to --acid--;

Column 9, line 3, change "about2" to --about 2--;

Column 9, line 21, before "ratio", delete "a";

Column 9, line 26, change "tracts," to --airway and--;

Column 9, line 34, change "ailments" to --ailment--;

Column 9, line 35, change "airway," to --airway and--;

UNITED STATES PATENT AND TRADEMARK OFFICE
CERTIFICATE OF CORRECTION

PATENT NO. : 7,060,691 B2
APPLICATION NO. : 10/267863
DATED : June 13, 2006
INVENTOR(S) : Giuseppe Petrigni et al.

It is certified that error appears in the above-identified patent and that said Letters Patent is hereby corrected as shown below:

Column 9 lines 2 and 16, change "1." to --1,--;

Column 9, line 5, change "1" to --1,--;

Column 9, line 12, change "3" to --3,--;

Column 9, lines 20 and 39, change "4" to --4,--;

Column 9, line 23, change "5" to --5,--;

Column 9, line 32 and column 10 line 36, change "9" to --9,--;

Column 10, line 3, change "Iwig" to --lung--;

Column 10, line 11, change "airway, and" to --airway,--;

Column 10, line 26, after "least" insert --one of --;

Column 10, line 30, change "13" to --13,--.

Signed and Sealed this

Seventeenth Day of October, 2006

JON W. DUDAS
*Director of the United States Patent and Trademark Office*